Figure 1:
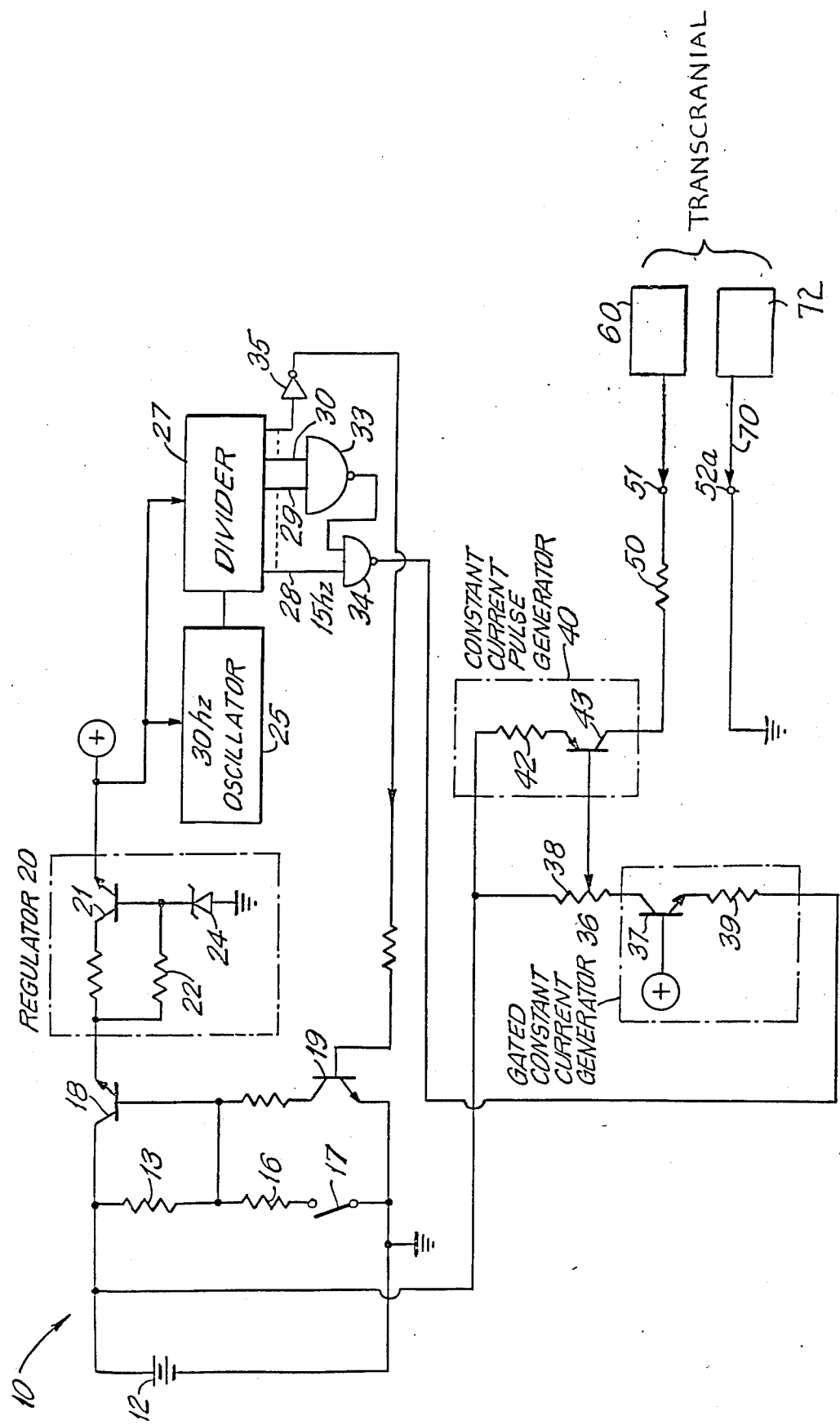

United States Patent [19]

Liss et al.

[11] Patent Number: 4,856,526

[45] Date of Patent: Aug. 15, 1989

[54] APPARATUS AND METHODOLOGY FOR TREATMENT OF HEADACHE SYNDROMES

[75] Inventors: Saul Liss; Bernard Liss, both of Glen Rock, N.J.

[73] Assignee: Pain Suppression Labs, Inc., Elmwood Park, N.J.

[21] Appl. No.: 21,140

[22] Filed: Mar. 3, 1987

Related U.S. Application Data

[63] Continuation-in-part of Ser. No. 926,971, Nov. 4, 1986, Pat. No. 4,784,142, and a continuation-in-part of Ser. No. 868,652, May 30, 1986, and a continuation-in-part of Ser. No. 860,745, May 7, 1986, said Ser. No. 926,971, is a continuation-in-part of Ser. No. 868,652, , which is a continuation-in-part of Ser. No. 860,745, , said Ser. No. 868,652, is a continuation-in-part of Ser. No. 640,104, Aug. 13, 1984, Pat. No. 4,627,438, and a continuation-in-part of Ser. No. 618,144, Jun. 7, 1984, Pat. No. 4,614,193, said Ser. No. 860,745, is a continuation-in-part of Ser. No. 640,104, , which is a continuation-in-part of Ser. No. 569,476, Jan. 9, 1984, Pat. No. 4,550,733, said Ser. No. 618,144, is a continuation-in-part of Ser. No. 569,476.

[51] Int. Cl.⁴ ............................................. A61N 1/30
[52] U.S. Cl. .................................................. 128/422
[58] Field of Search ............... 128/1 C, 419 R, 420 R, 128/421, 422, 423 R, 791

[56] References Cited

U.S. PATENT DOCUMENTS

| | | | |
|---|---|---|---|
| 3,762,396 | 10/1973 | Ballentine et al. | 128/791 |
| 3,902,502 | 9/1975 | Liss et al. | 128/422 |
| 4,537,195 | 8/1985 | McDonnell | 128/422 |
| 4,646,744 | 3/1987 | Capel | 128/423 R |

FOREIGN PATENT DOCUMENTS

| | | | |
|---|---|---|---|
| 3034657 | 4/1982 | Fed. Rep. of Germany | 128/420 R |
| 1350877 | 12/1963 | France | 128/1 C |

Primary Examiner—William E. Kamm
Attorney, Agent, or Firm—Hopgood, Calimafde, Kalil, Blaustein & Judlowe

[57] ABSTRACT

Headache modulator apparatus and methodology employs a transcutaneous electronic wave to reduce and control migraine and vascular headaches. A pair of electrodes is placed transcranially, i.e., a first contact electrode is placed at one side of the cranium and a second electrode is placed at the opposite side of the cranium of the head. An electronic current wave comprising relatively high frequency pulses with a low frequency amplitude modulation is then applied between the positive and negative electrodes.

8 Claims, 2 Drawing Sheets

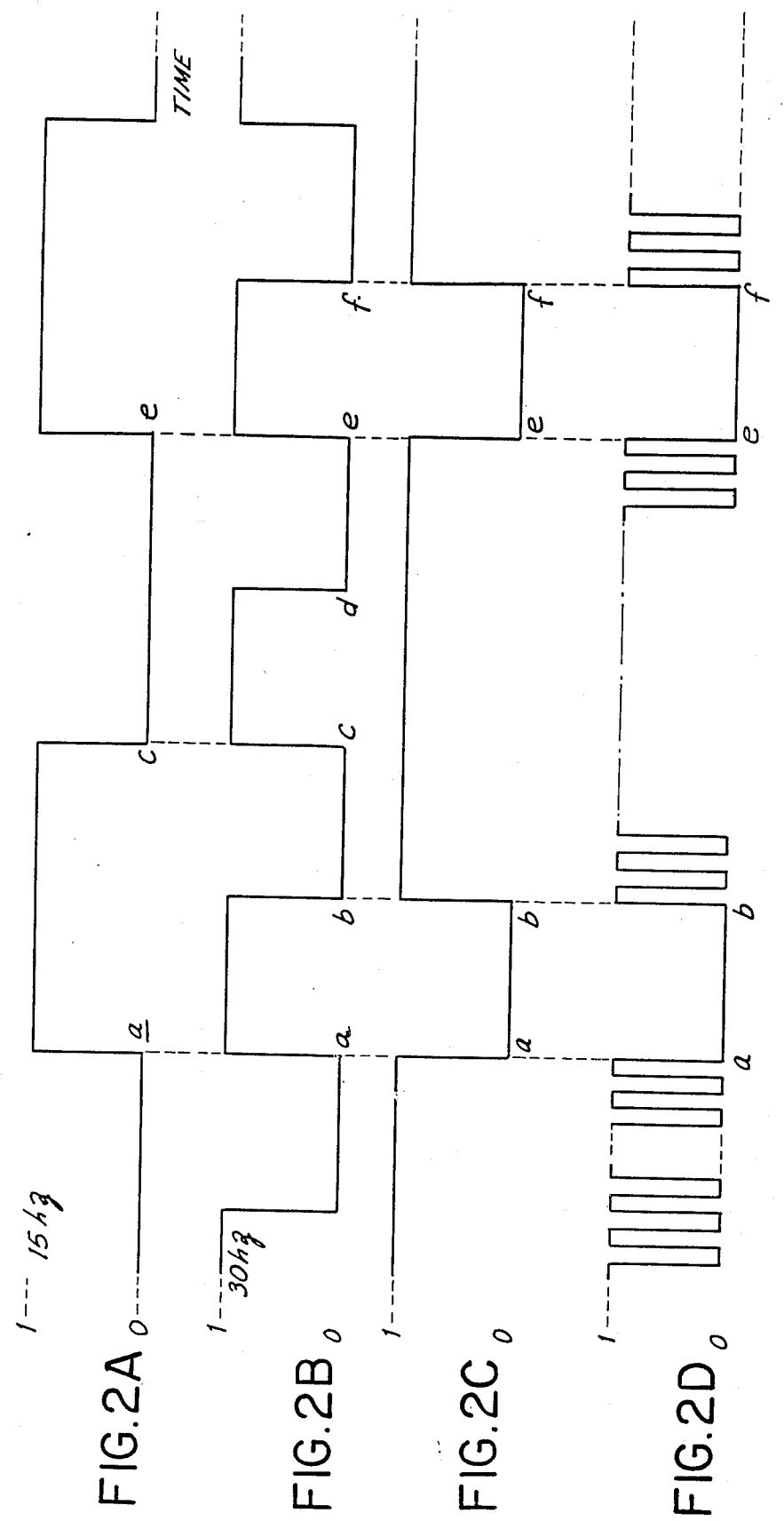

APPARATUS AND METHODOLOGY FOR TREATMENT OF HEADACHE SYNDROMES

CROSS REFERENCES TO RELATED CASES

This application is a continuation-in-part to applications: (1) 926,971 filed on Nov. 4, 1986, now U.S. Pat. No. 4,784,142 (2) 868,652 filed May 30, 1986 and (3) 860,745 filed May 7,1986.

Application (1) above is a continuation-in-part to applications (2) and (3) above.

Application (2) above is a continuation-in-part to applications (4) 640,104 filed Aug. 13, 1984 (now U.S. Pat. No. 4,627,438), and (5) 618,144 filed on June 7, 1984 (now U.S. Pat. No. 4,614,193).

Application (3) above is a continuation-in-part to application (4) above.

Applications (4) and (5) above are continuations-in-part to application (6) 569,476 filed Jan. 9, 1984 (now U.S. Pat. No. 4,550,733).

This invention relates to electronic pain suppression apparatus and methodology and, more specifically, to headache modulator apparatus and procedure for eliminating, reducing or controlling headache syndromes to specifically include those referred to as migraine or vascular. The word "migraine" as used hereinbelow represents both headache syndromes.

It is an object of the present invention to provide headache modulator apparatus and methodology for treating migraine headaches.

More specifically, an object of the present invention is the electronic treatment of migraine headaches in a safe, efficient and rapid manner to eliminate, reduce or control the headache and alleviate pain associated with the syndrome.

It is a further object of the present invention to provide electronic transcutaneous electronic nerve stimulating equipment operative at very low, milliampere current levels which relieves perceived pain and treats migraine headaches.

The above and other objects and features of the instant invention are realized in a specific illustrative migraine headache modulator and methodology which employs a transcutaneous electronic wave to reduce or control the headache and alleviate the pain associated with the condition. A pair of electrodes is placed transcranially. The pair of electrodes can be in the form of a headset. A first contact electrode is placed at one side of the patient's head, e.g., over one temporal area and a second negative contact electrode is placed at the opposite side of the patient's head, e.g., over the opposite temporal area. Advantageously, the first contact electrode is placed over the proximal aspect of one temporal bone area and the second contact electrode is placed over the proximal aspect of the opposite temporal bone area. An electronic current wave comprising relatively high frequency pulses with a low frequency modulation is then applied from the positive to the negative electrodes.

The above and other features and advantages of the instant invention will become more clear from the following detailed description of a specific illustrative embodiment thereof, presented hereinbelow in conjunction with the accompanying drawing, in which:

FIG. 1 is a schematic diagram of an electronic migraine headache syndrome modulator apparatus embodying the principles of the present invention; and FIGS. 2A through 2D are wave forms illustrating the operation of the FIG. 1 apparatus.

The apparatus of the instant invention has been found to relieve the symptoms of migraine/vascular headaches with a relatively low level current and without chemical intervention.

To illustrate performance of the instant invention in overview, the apparatus in FIG. 1 is utilized to treat the symptoms associated with the diseased state of a patient who is suffering from migraine headaches. A pair of electrodes is placed transcranially, e.g., bitemporally. A first contact electrode 60 (FIG. 1) is placed at one side of the head and a second contact electrode 72 (FIG. 1) is placed at the opposite side of the head. The treatments should be from ten to twenty minutes.

An electronic wave (depicted in FIG. 2D) is applied between the first electrode 60 and the second electrode 72. The wave form of FIG. 2D comprises a low level (typically less than 4 milliamperes) pulse train of relatively high frequency, e.g., between 12 and 20 khz modulated in amplitude by a relatively low frequency wave in the range of 8 to 20 hz. The low frequency wave is preferably non-symmetrical (that shown in FIG. 2D), for example, characterized by a 3:1 duty cycle, being on three quarters of the time and off one quarter of the recurring period. For concreteness only and without limitation, it will hereinafter be assumed that the high frequency pulse occurs at a 15 khz rate and 1-1.5 m.a. level, while being subject to a 15 hz modulation with a 3:1 duty factor.

It has been found that the wave of FIG. 2D is effective to block the pain perceived and relieve headaches. The exact mechanism causing elimination of the pain associated with migraine/vascular headaches is still unknown although it is believed to follow from changes in levels of certain neurotransmitter such as serotonin and endorphins, in response to the low frequency modulation envelope introduced into the body.

While the precise operative mechanism may be the subject of debate, the fact of the headache pain relief is not.

The FIG. 1 electronic apparatus 10 for generating and applying the wave form of FIG. 2D will now be specifically considered. A battery 12 is connected to a PNP series pass transistor 18 which, in turn, selectively passes the voltage from battery 12 through a voltage regulator 20 to form the positive direct current voltage supply for the apparatus 10 electronics. The unit is first turned on by momentarily closing a power-on switch 17. This applies a low voltage to the base of PNP transistor 18, turning that device on and effectively coupling the potential of battery 12 to a series pass transistor 21 in the voltage regulator 20. Because the final output of a counter or divider chain 27 is initially low on power turn on, the resulting high output of inverter 35 applies a high potential to the base of transistor 19, turning it on and thereby latching PNP transistor 18 to its conductive condition when switch 17 is released. This maintains the electronic apparatus on for a desired period which is determined by the frequency of an oscillator 25 and the division factor of the divider 27, i.e., the period required for the most significant stage of the counter 27 to reach its high or binary "1" state. The switched power supply assures that the electronic apparatus is not inadvertently left on to unduly discharge the battery 12.

The regulated output of battery 12 applied through PNP transistor 18 is converted to a lower regulated value by the regulator 20. Regulator 20 is per se well known and includes the series pass PNP transistor 21 having a constant voltage applied to the base thereof by a Zener diode 24 energized by a resistor 22. The constant potential output of regulator 20, which serves as the supply voltage for much of the remaining electronics of FIG. 1, is the characteristic reverse excitation voltage of Zener diode 24 less about 7/10 of a volt for the base-emitter drop of transistor 21.

As above noted, the active power supply interval for circuit 10 of the drawing is fixed and present to a specific period. The above-discussed time out circuitry is employed to assure that the unit is not inadvertently left on. Many ways of achieving this result will be readily apparent to those skilled in the art. For example, a variable time out may be provided by employing a switch to connect the input of inverter 35 to varying ones of the more significant stage outputs of the pulse counter chain 27. Yet further, separate electronic or electromechanical timer apparatus, fixed or variable, all per se well known, may be employed to supply a positive potential to the base of transistor 19 for the desired "on" period; and to switch off the base drive to transistor 19, thereby turning off series pass transistor 18, when the desired operative period has passed.

A time base oscillatory 25 supples an input to the pulse counter or divider chain 27. The frequency of oscillator 25 is chosen for convenience to be an integral multiple of the pulse frequency (FIG. 2D) desired for delivery to the patient. For the assumed 15 khz desired frequency, a 30 khz oscillation repetition rate may be usefully employed by oscillatory 25, such that the 15 khz signal is derived at a divide-by-two tap 28 of divider chain 27. The 15 khz signal is supplied as one input to a NAND gate 34, the output of which corresponds to the ultimately desired wave of FIG. 2D. Output 29 and 30 of divider 27 are supplied as inputs to a NAND gate 33, the output of which is supplied as a second input to the NAND gate 34. The output 29 of divider 27 supplies the 30 hz wave of FIG. 2B (pulse division factor 1,000 at tap 29), while the 15 hz wave of FIG. 2A is supplied at a divider output 30 (divider factor: 2,000). Logic gate 33 generates the output wave of FIG. 2C, being at its high or Boolean "1" value when either of the waves of FIGS. 2A or 2B is low (i.e., preceding the time a, during the interval b-e, and following time f). Correspondingly, during the periods a-b and e-f when the output at divider 27 taps 29 and 30 are both high, the output of gate 33 is low (Boolean "0" value).

The wave form of FIG. 2C is supplied as one input to the gate 34 together with the 15 khz pulse train at the divide-by-two counter 27 output port 28. Accordingly, the output of NAND gate 34 switches between its high and low state during the periods when the FIG. 2C wave is high, i.e., preceding time a, during the interval b-e, following the time f, and so forth for the recurring pattern illustrated by FIGS. 2A-2D.

The voltage wave from of FIG. 2D is converted to a current in the milliampere range for application to the patient by the following circuitry of FIG. 1. As a first matter, a gated constant current generator 36 passes a gated current (either off or of a fixed value) through a potentiometer 38 under control of the output of the NAND gate 34. When the output of NAND gate is low, a transistor 37 in constant current generator 36 is on and a current substantially given by the positive potential output of regulator 20 (applied to the base of transistor 37) less a 7/10 of a volt base emitter drop for the transistor 37, divided by the resistance value of the resistance 39 in the emitter circuit of transistor 37. The voltage at the variable tap of the potentiometer 38 is supplied to the base of a PNP transistor 43 of a constant current pulse generator 40. The output of pulse generator 40 is a current which switches between its off (zero current) state, and a value given by the voltage at the potentiometer 38 tap, less a diode drop for the emitter-base of transistor 43, divided by the resistance value of resistor 42 connected in the emitter circuit of the PNP device 43. This pulsed current output of pulse generator 40 corresponds in wave form to FIG. 2D, and is at a level, determined by the setting of potentiometer 38, in the low milliampere range. It is this current pulse which is ultimately delivered to the patient to provide the requisite relief of symptoms.

In a typical application the patient is provided with the potentiometer 38. The potentiometer is first turned up so that the administered current pulses provide a noticeable tingling sensation on the patient's skin surface. The patient is then instructed to turn down the potentiometer adjustment until the sensation just disappears. The will provide the amount of transcutaneous electronic stimulation to treat the symptoms associated with the patient's disease. The potentiometer setting may be adjusted to the patient as required.

The current pulses from generator 40 pass through a protective, series limiting resistor 50 to an output terminal 51 to the electrode 60. The current transcutaneously passes into the patient, flows through the patient, and returns to eleectronic ground via the electrode 72. Electrodes 60 and 72 are placed transcranially. Electrode 72 is connected to electronic system ground via lead 70 and apparatus terminal port 52a.

To illustrate the efficacy of the instant invention in reducing migraine/vascular headaches, the above described apparatus and methodology was employed from May, 1984 to July, 1986 under the supervision of Dr. David R. Coddon. An open clinical use study was initiated with the use of the apparatus of the invention. According to protocol, patients were randomly selected for treatment. Patients were limited to headache patients in various categories defined below. Two-hundred and eighty-six (286) patients in the following categories were studied:

1. Sixty-eight (68) patients were diagnosed as having Migraine Headache Syndrome. These patients had a history of carsickness in childhood, a family history of migraine and various clinical features associated with migraine.

2. Fifty (50) patients were diagnosed as having Vascular Headache Syndrome or so-called Tension, Muscle Contraction Headache. These patients were typically awakened with headaches, usually located over the forehead or in the temples without any other associated symptoms.

3. Fifty-six (56) patients were diagnosed as having Mixed Migraine and Vascular Headache Syndrome. These patients had a combination of the features listed in categories 1 and 2.

4. Twenty-six (26) patients were diagnosed as having Post-Traumatic Headache Syndrome (including whiplash injuries). These patients had whiplash injuries or direct closed injuries from auto accidents or from something striking their heads.

5. Seven (7) patients were diagnosed as having Conversion Reaction Headache Syndrome, i.e., where the symptom of headache was a substitute for an unpleasant experience with which the patient was unable to cope.

6. Fourteen (14) patients were diagnosed as having Depressive Reaction Headache Syndrome. These patients were clearly depressed with the concomitant features of disturbance of sleep, loss of appetite and interest, difficulty in concentration and non-specific headaches.

7. Fourteen (14) patients were diagnosed as having Toxic Metabolic Headache Syndrome. These patients were clearly taking excessive amounts of medications, usually Fiorinal or Cafergot, usually producing a rebound headache.

8. Sixteen (16) patients were diagnosed as having Hypertensive Headache Syndrome. These patients had headaches associated with clear-cut evidence of hypertension responsive to the appropriate medications which lowered their pressure, with some improvement of their headaches. 9. Twenty-one (21) patients were diagnosed as having Chronic Headache Syndrome which was unresponsive to any form of treatment. These patients had intractable headaches for over twenty years which were unresponsive to all forms of therapy and usually followed some traumatic incident. These patients had previously been seen by numerous physicians.

10. Eight (8) patients were diagnosed as having "Non-Headache" Headache Syndrome. These patients constantly complained of headaches which were unresponsive to all forms of therapy. These individuals were totally functional, however.

11. Six (6) patients were diagnosed as having Post-infectious (post-viral) Headache Syndrome. These patients had a documented case of infectious mononucleosis in the presence of the Epstein-Barr virus.

Pregnant women, patients with seizure disorders, carotid artery disease and those with pacemakers were excluded from the study.

It is important to emphasize that the natural history of headaches in all patients is highly individual. Thus, the major concern of the study was that of evaluating the device for its effectiveness in a usual practice setting.

Each patient selected for treatment with the NTM was given four training sessions, two per week, each typically lasting between 10 and 20 minutes. During these visits the patients were instructed in the use of the device. The placement of the contacts was transcranial (bitemporal) with the black electrode applied first to the left side, the red electrode applied to the right side. Afterwards, the contacts were reversed for about ten minutes. The patients were instructed to use the apparatus as many times as they wanted per day for 10-20 minute sessions regardless of the severity of their headaches. The device was turned either to its full amperage level (4 milliamperes) or to patient tolerance, i.e., less than 4 milliamperes.

The population presented was such that many of the patients, children and adults (ages 8-76), were quite receptive to trying a non-drug therapy. All of the patients had variations in the severity of their attacks and for the purposes of this study, the severity of the attacks was graded in a very simple manner, namely:

1. mild headache where the patient was able to carry on activities without any interference with level of performance;

2. moderately severe headache, where the patient was more aware of the headache and had some difficulty in concentrating or performing usual activities; and 3. severe headaches, where there was great interference or total incapacitation in performance or usual activities.

This last group included those patients with acute migraine attacks.

The patients were divided approximately equally between the sexes. Based on patient follow-up visits and discussions, it was apparent that a majority of the patients were using the unit only during headache attacks, though some 85 patients in all categories were successfully using it prophylactically.

Migraine Headache Syndrome

1. Of the 68 patients, 75% of 51 patients with migraine headache syndrome were able to successfully use the NTM to completely abort or greatly relieve their migraine attacks.

2. Complete relief of migraine attacks was observed in 6 patients during their office visits.

3. About 12 of the migraine headache patients were unable to stop or alter their attacks with the use of the NTM.

Vascular Headache Syndrome Mixed Migraine & Vascular Headache Syndrome

1. Approximately 80% or 85 patients of the total 106 patients in these categories were able to successfully abort or greatly diminish the intensity of their attacks with the NTM.

Chronic Headache Syndrome Unresponsive to Any Form of Treatment and "Non-Headache" Headache Syndrome Twenty-nine (29) patients were unresponsive to treatment, as they had been to other treatments.

In general, four (4) patients complained of some transient nausea during their initial use of the NTM. This disappeared on continued use.

The use of the device also appeared to make some patients, i.e., seven (7) patients more responsive to biofeedback therapy.

Two patients described an increase in headache severity due to the use of the NTM, on initial use. On continued use, however, the patients gained relief.

Five (5) patients noticed some skin redness at the site of the contact points (temples) which subsided and disappeared soon after use. No other side effects were noted.

The success rate in terms of efficacy on a sustained basis has remained consistent in the patients who have been followed up for a period of anywhere from 3 months to two years. In a review of the data over the past two years, it has become evident that the results have been consistent such that the use of the apparatus and methodology of the invention in a large number of headache patients is a well established mode of therapy and can often be considered the treatment of choice.

An equally effective method was found to be as follows:

1. The electrodes were placed bitemporally as described above. Stimulation was for about ten minutes at far above threshold levels, i.e., near the point at which the patient said it was uncomfortable.

2. The contacts were then placed in reverse configuration for about ten minutes.

3. A maximum level of stimulation for acute headache attack was utilized.

4. A maximum of three reversals (40 minutes total) were performed per use with a two hour minimum time between stimulations.

Based on the foregoing data, the apparatus and methodology of the invention was demonstrated to be extremely effective in treating a variety of headache syndromes in a very large number of patients of all age groups.

The above described apparatus and methodology are merely illustrative of the principles of the present invention. Numerous modifications and adaptions thereof will be readily apparent to those skilled in the art without departing from the spirit and scope of the present invention.

What is claimed is:

1. A method (for relieving pain and symptoms associated with migraine and vascular headache syndromes) comprising securing a pair of electrodes wherein a first contact electrode is secured at one side of the head and a second contact electrode is secured at the opposite side of the patient's head and supplying an electronic current wave comprising a high frequency electrical wave bearing a low frequency amplitude modulation to said first and said second electrodes.

2. The method of claim 1, wherein the step of securing a pair of electrodes further comprises securing said first electrode over one temporal area and securing said second electrode over the opposite temporal area.

3. The method as in claim 1, wherein the step of securing a pair of electrodes further comprises securing said first electrode over a proximal aspect of one temporal bone area and securing said second electrode over a proximal aspect of the opposite temporal bone area.

4. The method as in claim 1, wherein the frequency of said high frequency electrical wave is in the range of 12-20 khz, wherein said low frequency modulation is in the range 8-20 hz, and wherein said wave does not exceed about 4 milliamperes.

5. The method as in claim 1, wherein said amplitude modulation is non-symmetrical.

6. A method (for relieving pain and symptoms associated with migraine and vascular headache syndromes) comprising securing a pair of electrodes transcranially on a subject's head and supplying an electronic current wave comprising a high-frequency electrical wave bearing a low-frequency amplitude modulation to said pair of electrodes.

7. The method of claim 6, wherein said high frequency electrical wave has a frequency range of 12-20 kHz, and said low-frequency amplitude modulation has a frequency range of 8-20 Hz, and said wave does not exceed about 4 milliamperes.

8. The method of claim 6, wherein said amplitude modulation is non-symmetrical.

* * * * *